(12) United States Patent
Zuo et al.

(10) Patent No.: US 9,133,138 B2
(45) Date of Patent: Sep. 15, 2015

(54) USE OF A QUINAZOLINE COMPOUND IN PREPARING A MEDICAMENT AGAINST FLAVIVIRIDAE VIRUS

(75) Inventors: Jianping Zuo, Shanghai (CN); Youhong Hu, Shanghai (CN); Wei Tang, Shanghai (CN); Bo Chao, Shanghai (CN); Xiankun Tong, Shanghai (CN); Dewen Li, Shanghai (CN); Feihong Ji, Shanghai (CN); Peilan He, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 4 days.

(21) Appl. No.: 13/992,870

(22) PCT Filed: Dec. 2, 2011

(86) PCT No.: PCT/CN2011/083357
§ 371 (c)(1),
(2), (4) Date: Jun. 10, 2013

(87) PCT Pub. No.: WO2012/075908
PCT Pub. Date: Jun. 14, 2012

(65) Prior Publication Data
US 2013/0261139 A1    Oct. 3, 2013

(30) Foreign Application Priority Data
Dec. 9, 2010   (CN) .......................... 2010 1 0581618

(51) Int. Cl.
*A61K 31/517* (2006.01)
*C07D 239/95* (2006.01)
*C07D 401/12* (2006.01)
*C07D 403/12* (2006.01)

(52) U.S. Cl.
CPC ............ *C07D 239/95* (2013.01); *A61K 31/517* (2013.01); *C07D 401/12* (2013.01); *C07D 403/12* (2013.01)

(58) Field of Classification Search
CPC .................................................. A61K 31/517

USPC ....................................................... 514/266.4
See application file for complete search history.

(56) References Cited

U.S. PATENT DOCUMENTS

| 7,629,340 | B2 | 12/2009 | Schmitz et al. | |
| 2001/0014679 | A1* | 8/2001 | Tang et al. | ............... 514/252.17 |
| 2007/0265262 | A1 | 11/2007 | Schmitz et al. | |

FOREIGN PATENT DOCUMENTS

| WO | WO 9418980 | 9/1994 |
| WO | WO 00/04901 | 2/2000 |
| WO | WO 2007/070556 | 6/2007 |
| WO | WO 2007/080401 | 7/2007 |

OTHER PUBLICATIONS

International Search Report for PCT/CN2011/083357 mailed Mar. 8, 2012.
Stevens et al. "The Medicinal Chemistry of Dengue Fever." Journal of Medicinal Chemistry Perspective, vol. 52, No. 24, Dec. 24, 2009, pp. 7911-7926.
Supplementary European Search Report issued in European Application No. 11847845 dated Apr. 24, 2014.

* cited by examiner

*Primary Examiner* — Shengjun Wang
(74) *Attorney, Agent, or Firm* — Nixon & Vanderhye P.C.

(57) ABSTRACT

Disclosed is a use of a quinazoline compound of Formula I having 2,4-diaminoquinazoline as a parent nucleus in preparation of a medicament for treating diseases caused by flaviviridae infection, especially a use in combating Hepatitis C virus infection and Dengue fever virus infection.

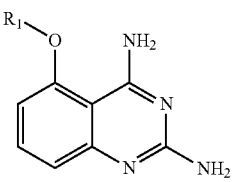

4 Claims, No Drawings

USE OF A QUINAZOLINE COMPOUND IN PREPARING A MEDICAMENT AGAINST FLAVIVIRIDAE VIRUS

This application is the U.S. national phase of International Application No. PCT/CN2011/083357 filed 2 Dec. 2011 which designated the U.S. and claims priority to CN 201010581618.3 filed 9 Dec. 2010, the entire contents of each of which are hereby incorporated by reference.

TECHNICAL FIELD

The present invention belongs to the field of materia medica, and relates to a medicinal use of a class of compounds having 2,4-diaminoquinazoline as the backbone, and more particularly, to a use of 2,4-diaminoquinazoline compounds in preparation of a medicament for treating diseases caused by flaviviridae virus, and in particular, to a use of the compounds against Hepatitis C virus and anti-Dengue fever virus.

BACKGROUND ART

Viruses are the smallest pathogenic microorganism, and viral infectious diseases have been one of the major diseases threatening human health, which are characterized by high incidence, fast spread, wide epidemic and great variability. Flaviviridae comprises three virus genera, which are Flavivirus, Pestivirus and Hepacivirus, and include over 60 viruses in total.

Dengue fever virus (DV) belongs to positive strand RNA virus of Flavivirus of Flaviviridae, and has 4 serotypes. Classical dengue fever (DF) and Dengue henorrhagic fever/Dengue Shock Syndrome (DHF/DSS) caused by mosquito-borne transmission are acute infectious diseases, the pathogen thereof may cause a number of diseases in humans, resulting in death in severe cases. Such diseases are widely distributed, and DF cases are greatly increasing recently. Such fatal infectious diseases have threatened the health of one third of the global population, and have become the important public health problems in Southeast Asia, Pacific islands, Caribbean and Central and South America.

At present, there have been no effective vaccines to prevent Dengue fever and no specific antiviral drugs to effectively treat Dengue fever in the world. Because of the particularity of diseases caused by DV, i.e., the antibody dependent enhancement and viral evolutionary mutation of DV infection, the research on DV vaccines has not made a significant breakthrough for many years.

Hepatitis C virus (HCV) belongs to Hepacivirus of Flaviviridae, and is a single-strand positive strand RNA virus with spherical viral particle. In 1989, Hepatitis C virus was identified as pathogene HCV for transfusion-associated non-A, non-B hepatitis, which may cause many clinical symptoms, most of them are benign or subacute ones. Symptom of chronic hepatic injury for many patients may not appear until 10-30 years after infected.

Researches on related drugs are blocked due to lack of proper experiment systems and animal models. So far, there is no vaccine or treatment method which can be used to treat Hepatitis C virus of all subtypes.

Under such circumstances, it is particularly important to develop drugs against Flaviviridae viruses, particularly Dengue fever virus and Hepatitis C virus, with low toxicity, high effectiveness and low price.

DISCLOSURE OF THE INVENTION 2,4-diaminoquinazoline compounds have been found through researches to have activities against Dengue fever virus and Hepatitis C virus.

Therefore, one object of the present invention is to provide a use of 2,4-diaminoquinazoline compounds in manufacturing a medicament for treating diseases caused by flaviviridae virus infection.

Another object of the present invention is to provide a pharmaceutical composition for treating diseases caused by flaviviridae virus, especially Dengue fever virus and Hepatitis C virus.

To achieve the above objects of the present invention, in an aspect of the present invention, provided is a use of a quinazoline compound of the following formula I or a physiologically acceptable salt thereof in manufacturing a medicament against flaviviridae virus, especially Hepatitis C virus and Dengue fever virus,

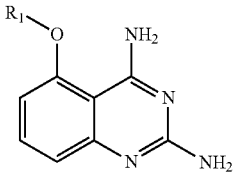

I wherein, $R_1$ is hydrogen, unsubstituted or substituted C1-C10 alkyl, unsubstituted or substituted C3-C10 cycloalkyl, trifluoromethyl, unsubstituted or substituted phenyl, unsubstituted or substituted heterocyclic group, or unsubstituted or substituted fused ring group;

the substituents are selected from the group consisting of C1-C10 alkyl, C1-C10 alkoxy, halogen, hydroxy, nitro, carboxy, C6-C10 aryl, phenolic group, amino, amino substituted with C1-C10 hydrocarbyl, heterocyclic group and trifluoromethyl;

the heterocyclic group is a 3- to 7-membered monocyclic ring or a 8- to 10-membered bicyclic ring, which may contain 1 to 3 heteroatoms selected from the group consisting of N, O and S.

Most preferably, the quinazoline compound of the present invention is selected from the group consisting of:

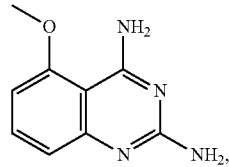

Yhhu-0967

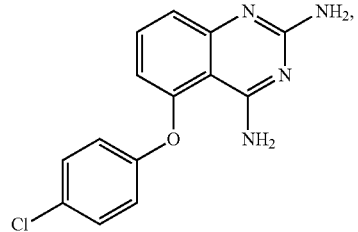

Yhhu-0968

Yhhu-0969
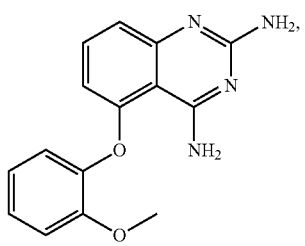
Yhhu-0970
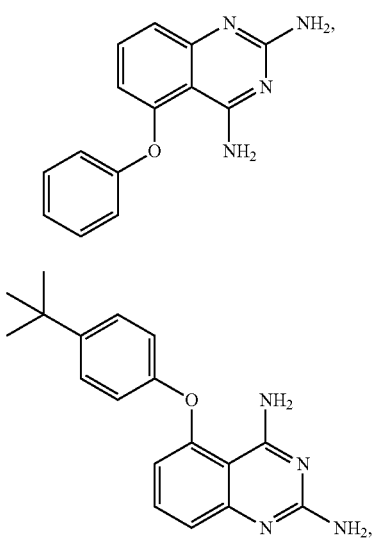
Yhhu-1035
Yhhu-1036
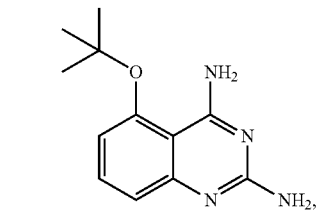
Yhhu-1041
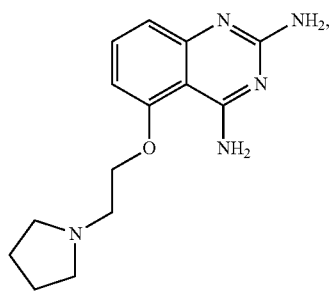
Yhhu-1046
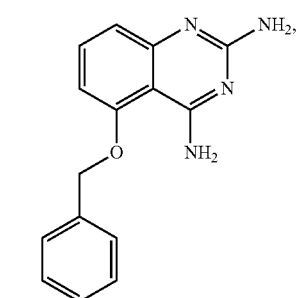
Yhhu-1053
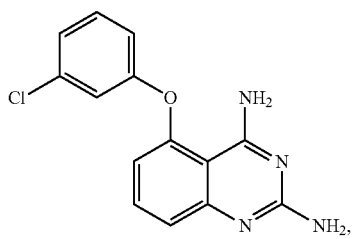
Yhhu-1056
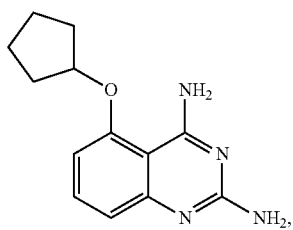
Yhhu-1145
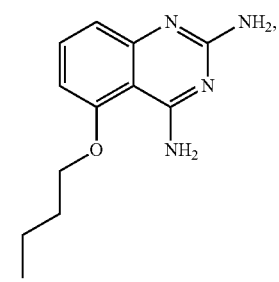
Yhhu-1146
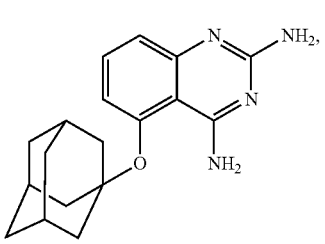
Yhhu-1147
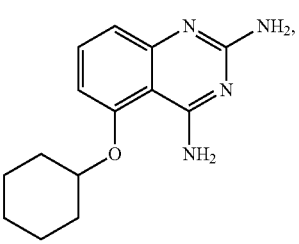
Yhhu-1148
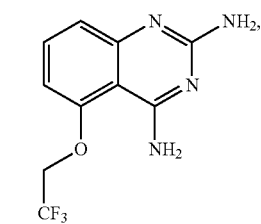

Yhhu-1149 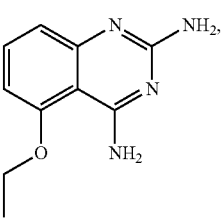

Yhhu-1150 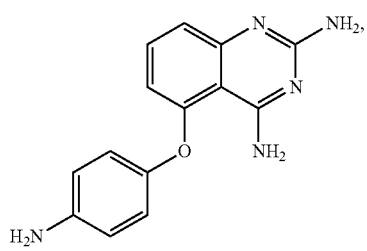

Yhhu-1151 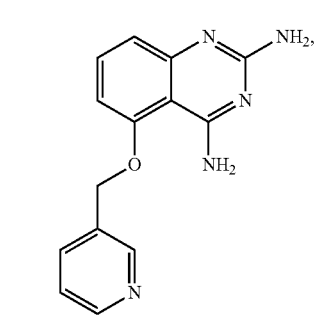

Yhhu-1152 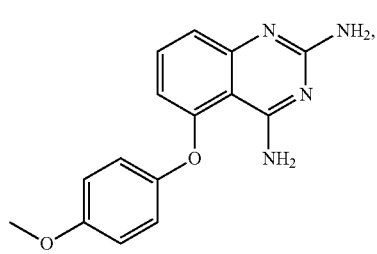

Yhhu-1411 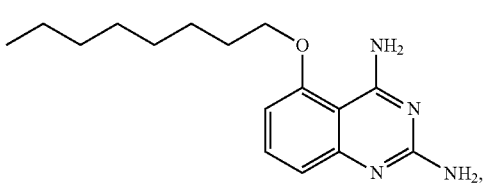

Yhhu-1412 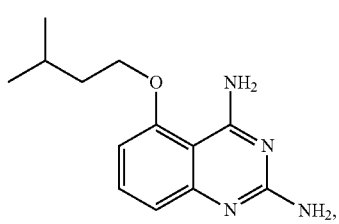

Yhhu-1413 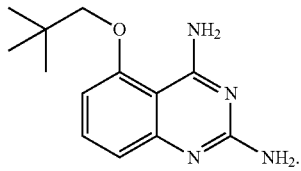

The quinazoline compound of the present invention may be prepared through the following method:

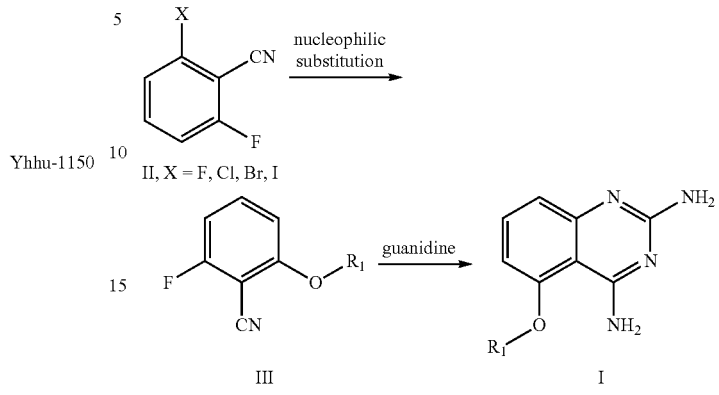

wherein, $R_1$ is defined as above.

The method comprises the following steps:

step (1): a compound of formula II was incorporated with a corresponding alkoxy substituent via nucleophilic substitution to give a compound of formula III;

step (2): a compound of formula III was cyclized with guanidine under heating to give a compound of formula I;

In the above step (1), the reaction condition in which the compound of formula II was incorporated with a corresponding alkoxy substituent via nucleophilic substitution is a conventional selection for those skilled in the art. In general, the nucleophilic substitution may be conducted under alkaline or neutral condition. Said alkaline is well-known to those skilled in the art, such as, potassium carbonate, sodium carbonate, sodium hydride, sodium hydroxide, triethylamine and the like.

In the above step (2), the reaction condition in which the compound of formula III was cyclized with guanidine under heating to give a compound of formula I is a conventional selection for those skilled in the art. In general, the reaction may be conducted under alkaline or neutral condition. Said alkaline is well-known to those skilled in the art, such as, potassium carbonate, sodium carbonate, sodium bicarbonate, sodium hydroxide, triethylamine and the like. The heating condition is well-known to those skilled in the art, such as, it can be heated to 120° C. to 180° C. or is heated by microwave.

The quinazoline compound of the present invention includes the physiologically acceptable salt thereof, and the physiologically acceptable salt of the quinazoline compound may be prepared by dissolving the compound in an alcoholic solution saturated by the corresponding acid. For example, the quinazoline compound of the present invention may be dissolved in a methanol solution saturated by HCl, stirred for 3 h at room temperature and then evaporated off the solvent to prepare the corresponding hydrochloride salt.

Another aspect of the present invention provides a pharmaceutical composition against flaviviridae virus, especially Dengue fever virus and Hepatitis C virus, which comprises a therapeutically effective amount of the quinazoline compounds of the formula I and pharmaceutically acceptable carriers.

The pharmaceutically acceptable carriers refer to the conventional pharmaceutical carriers in the pharmaceutical field, for example, a diluent, such as, water and the like; a filler, such as, starch, sucrose and the like; an binder, such as, a cellulose derivative, alginate, gelatin, polyvinylpyrrolidone; a moistening agent, such as, glycerin; a disintegrating agent, such as, agar, calcium carbonate and sodium bicarbonate; a sorbefacient, such as, a quaternary ammonium compound; a surfactant, such as, hexadecanol; an adsorption carrier, such as, kaolin and bentonite; a lubricant, such as, talcum, calcium stearate, magnesium stearate, polyethylene glycol and the like. Furthermore, other adjuvants, such as, a flavouring agent and a sweetening agent, may also be added to the pharmaceutical composition.

The quinazoline compound of the present invention may be administered in the form of a composition to a patient in need orally, rectally or extraintestinally. For oral administration, it may be formulated into a conventional solid preparation, such as, tablet, powder, granule, capsule and the like; or into a liquid preparation, such as, water or oil suspension, or other liquid preparations, such as, syrup and the like. For extraintestinal administration, it may be formulated into a solution, water or oil suspension and the like for injection.

Biotic experiments on the inhibitive activity of the quinazoline compound of the present invention or physiologically acceptable salt thereof against flaviviridae virus (Hepatitis C virus and Dengue fever virus) on cell model show that they have a very high inhibitive activity against flaviviridae virus and can be used to prepare a medicament for treating diseases caused by infection of flaviviridae virus, especially Hepatitis C virus and Dengue fever virus.

BEST MODE FOR CARRYING OUT THE INVENTION

The following examples specified the preparation of the compounds of the present invention, and the use of the biologic activity thereof for prohibiting flaviviridae virus, especially Hepatitis C virus and Dengue fever virus, but the invention is not limited thereto.

Example 1

Preparation of Compound Yhhu-0967
(5-methoxy-2,4-diaminoquinazoline)

2.53 g (79.08 mmol) of methanol was dropped into 5.18 g (86.27 mmol) of 40% sodium hydride suspension in tetrahydrofuran (150 ml) at 0° C. and stirred for 10 min, followed by dropwise addition of 10.0 g (71.89 mmol) of 2,6-difluorobenzonitrile in tetrahydrofuran (100 ml). The reaction mixture as stirred at room temperature for 10 h to complete the reaction. 200 ml of water was added thereto to destroy the excess sodium hydride, and the reaction mixture was extracted with 500 ml of ethyl acetate. The organic layer was dried with anhydrous sodium sulfate and evaporated to dryness. The residue was passed through column chromatography to provide an intermediate. The intermediate and 17.41 g (143.78 mmol) of guanidine carbonate were heated to 140° C. in 300 ml of N,N-dimethylacetamide and stirred for 8 h to complete the reaction. The reaction mixture was evaporated to dryness, then diluted with 200 ml of water and extracted with 400 ml of dichloromethane. The organic layer was dried with anhydrous sodium sulfate and then evaporated to dryness. The residue was passed through column chromatography to proved 9.85 g of compound Yhhu-0967 with a total yield of 72% in the two steps).

1H NMR (300 MHz, CHLOROFORM-d) d ppm 3.97 (s, 3H) 4.83 (br. s., 2H) 5.68 (br. s., 1H) 6.53 (d, J=8.06 Hz, 1H) 7.03 (d, J=8.55 Hz, 1H) 7.45 (t, J=8.18 Hz, 2H)

Example 2

Preparation of Compound Yhhu-0968
(5-(4-chlorophenoxy)-2,4-diamino quinazoline)

10.0 g (71.89 mmol) of 2,6-difluorobenzonitrile, 10.17 g (79.08 mmol) of 4-chlorophenol and 19.87 g (143.78 mmol) of potassium carbonate were added into 300 ml of N,N-dimethylformamide, and stirred at 50° C. for 10 h to complete the reaction. The reaction mixture was evaporated to dryness, diluted with 200 ml water and extracted with 400 ml ethyl acetate. The organic layer was dried with anhydrous sodium sulfate and evaporated to dryness. The residue was passed through column chromatography to provide an intermediate. The intermediate and 17.41 g (143.78 mmol) of guanidine carbonate were heated to 140° C. in 300 ml of N,N-dimethylacetamide and reacted for 8 h to complete the reaction. The reaction mixture was evaporated to dryness, diluted with 200 ml of water and extracted with 400 ml of dichloromethane. The organic layer was dried with anhydrous sodium sulfate and evaporated to dryness. The residue was passed through column chromatography to provide 13.7 g of compound Yhhu-0968 with a total yield of 67% in the two steps).

1H NMR (300 MHz, CHLOROFORM-d) ppm 2.06 (br. s., 2H) 5.09 (br. s., 2H) 6.33 (dd, J=7.98, 1.10 Hz, 1H) 7.05-7.11 (m, 2H) 7.15 (dd, J=8.53, 1.10 Hz, 1H) 7.34-7.43 (m, 3H)

Example 3

Preparation of Compound Yhhu-0969
(5-(2-methoxyphenoxy)-2,4-diaminoquinazoline)

The title compound was prepared in the same manner as that in example 2, except that 2-methoxyphenol was used to replace 4-chlorophenol.

1H NMR (300 MHz, CHLOROFORM-d) ppm 5.26 (s, 3H) 7.54 (d, J=7.98 Hz, 1H) 7.67 (br. s., 2H) 8.36 (d, J=8.25 Hz, 1H) 8.54 (td, J=7.50, 1.79 Hz, 1H) 8.62-8.85 (m, 4H) 8.89 (br. s., 1H)

Example 4

Preparation of Compound Yhhu-0970
(5-phenoxy-2,4-diaminoquinazoline)

The title compound was prepared in the same manner as that in example 2, except that phenol was used to replace 4-chlorophenol.

1H NMR (300 MHz, CHLOROFORM-d) ppm 4.83 (br. s., 2H) 6.30-6.37 (m, 1H) 7.13 (t, J=7.84 Hz, 3H) 7.21-7.29 (m, 1H) 7.36 (t, J=8.25 Hz, 1H) 7.39-7.47 (m, 2H)

Example 5

Preparation of Compound Yhhu-1035
(5-(4-tert-butylphenoxy)-2,4-diaminoquinazoline)

The title compound was prepared in the same manner as that in example 2, except that 4-tert-butylphenol was used to replace 4-chlorophenol.

1H NMR (300 MHz, CHLOROFORM-d) ppm 1.35 (s, 9H) 3.56 (br. s., 1H) 4.80 (br. s., 2H) 5.57 (br, s, 1H) 6.35 (d, J=8.25 Hz, 1H) 7.02-7.13 (m, 3H) 7.35 (t, J=8.11 Hz, 1H) 7.43 (d, J=8.80 Hz, 2H)

Example 6

Preparation of Compound Yhhu-1036 (5-tert-butoxy-2,4-diaminoquinazoline)

The title compound was prepared in the same manner as that in example 1, except that 4-tert-butanol was used to replace methanol.

1H NMR (300 MHz, CHLOROFORM-d) ppm 1.54 (s, 9H) 4.87 (br. s., 2H) 5.62 (br. s., 1H) 6.76 (d, J=7.15 Hz, 1H) 7.08 (d, J=7.43 Hz, 1H) 7.41 (t, J=8.25 Hz, 1H) 7.79 (br. s., 1H)

Example 7

Preparation of Compound Yhhu-1041 (5-(2-(1-pyrrolidinyl)ethoxy)-2,4-diaminoquinazoline)

The title compound was prepared in the same manner as that in example 1, except that 2-(1-pyrrolidinyl)ethanol was used to replace methanol.

1H NMR (300 MHz, CHLOROFORM-d) ppm 1.70-1.89 (m, 4H) 2.49-2.69 (m, 4H) 2.95 (t, J=5.64 Hz, 2H) 4.22 (t, J=5.64 Hz, 2H) 5.34 (br. s., 2H) 5.68 (br. s., 1H) 6.56 (d, J=7.98 Hz, 1H) 7.05 (d, J=7.70 Hz, 1H) 7.45 (t, J=8.25 Hz, 1H) 8.56 (br. s., 1H)

Example 8

Preparation of Compound Yhhu-1046 (5-benzyloxy-2,4-diaminoquinazoline)

The title compound was prepared in the same manner as that in example 1, except that benzalcohol was used to replace methanol.

1H NMR (300 MHz, CHLOROFORM-d) ppm 5.16 (s, 2H) 5.53 (br. s., 2H) 6.11 (br. s., 1H) 6.62 (d, J=7.98 Hz, 1H) 7.03 (d, J=8.53 Hz, 1H) 7.28-7.49 (m, 6H) 7.57 (br. s., 1H)

Example 9

Preparation of Compound Yhhu-1053 (5-(3-chlorophenoxy)-2,4-diamino quinazoline)

The title compound was prepared in the same manner as that in example 2, except that 3-chlorophenol was used to replace 4-chlorophenol.

1H NMR (300 MHz, METHANOL-d4) ppm 6.46 (d, J=7.98 Hz, 1H) 7.05 (d, J=8.53 Hz, 1H) 7.12 (dd, J=8.11, 2.34 Hz, 1H) 7.25 (t, J=2.20 Hz, 1H) 7.28-7.34 (m, 1H) 7.42-7.54 (m, 2H)

Example 10

Preparation of Compound Yhhu-1056 (5-cyclopentyloxy-2,4-diaminoquinazoline)

The title compound was prepared in the same manner as that in example 1, except that cyclopentanol was used to replace methanol.

1H NMR (300 MHz, METHANOL-d4) ppm 1.81 (m., 4H) 2.00 (m, 4H) 5.00-5.10 (m, 1H) 6.67 (d, J=8.25 Hz, 1H) 6.86 (d, J=8.25 Hz, 1H) 7.45 (t, J=8.25 Hz, 1H)

Example 11

Preparation of Compound Yhhu-1145 (5-n-butoxy-2,4-diaminoquinazoline)

The title compound was prepared in the same manner as that in example 1, except that n-butanol was used to replace methanol.

1H NMR (300 MHz, DMSO-d6) ppm 0.94 (t, J=7.33 Hz, 3H) 1.38-1.50 (m, 2H) 1.71-1.87 (m, 2H) 4.11 (t, J=6.16 Hz, 2H) 5.99 (s; 2H) 6.54 (d, J=7.92 Hz, 1H) 6.75 (d, J=8.80 Hz, 1H) 7.25 (s, 2H) 7.34 (t, J=8.06 Hz, 1H)

Example 12

Preparation of Compound Yhhu-1146 (5 (1-adamantyloxy)-2,4-diaminoquinazoline)

The title compound was prepared in the same manner as that in example 1, except that 1-adamantanol was used to replace methanol.

1H NMR (300 MHz, CHLOROFORM-d) ppm 1.67 (d, J=1.93 Hz, 6H) 2.07 (m, J=2.75 Hz, 6H) 2.23 m, 4H) 5.08 (br. s., 2H) 5.64 (br. s., 1H) 6.83 (dd, J=7.98, 0.83 Hz, 1H) 7.13 (dd, J=8.39, 0.96 Hz, 1H) 7.42 (t, J=8.11 Hz, 1H) 7.99 (br. s., 1H)

Example 13

Preparation of Compound Yhhu-1147 (5-cyclohexyloxy-2,4-diaminoquinazoline)

The title compound was prepared in the same manner as that in example 1, except that cyclohexanol was used to replace methanol.

1H NMR (300 MHz, CHLOROFORM-d) ppm 1.31-1.54 (m, 2H) 1.54-1.71 (m, 2H) 1.72-1.88 (m, 2H) 2.02-2.21 (m, 2H) 2.49-2.85 (m, 2H) 4.42-4.56 (m, 1H) 5.22 (br. s., 2H) 5.65 (s, 1H) 6.57 (d, J=8.25 Hz, 1H) 7.01 (d, J=8.25 Hz, 1H) 7.43 (t, J=8.25 Hz, 1H) 7.80 (s, 1H)

Example 14

Preparation of Compound Yhhu-1148 (5-(2,2,2-trifluoroethoxy-2,4-diaminoquinazoline)

The title compound was prepared in the same manner as that in example 1, except that 2,2,2-trifluoroethanol was used to replace methanol.

1H NMR (300 MHz, DMSO-d6) ppm 4.97 (q, J=8.70 Hz, 2H) 6.23 (br. s., 2H) 6.68 (d, J=7.92 Hz, 1H) 6.88 (d, J=8.21 Hz, 1H) 6.96 (hr. s., 1H) 7.42 (t, J=8.06 Hz, 1H) 7.53 (br. s., 1H)

Example 15

Preparation of Compound Yhhu-1149 (5-ethoxy-2,4-diaminoquinazoline)

The title compound was prepared in the same manner as that in example 1, except that ethanol was used to replace methanol.

1H NMR (300 MHz, DMSO-d6) ppm 1.41 (t, J=7.04 Hz, 3H) 4.17 (q, J=7.13 Hz, 2H) 6.07 (s, 2H) 6.55 (d, J=7.92 Hz, 1H) 6.77 (d, J=8.50 Hz, 1H) 7.27-7.43 (m, 3H)

Example 16

Preparation of Compound Yhhu-1150 (5-(4-aminophenoxy)-2,4-diaminoquinazoline)

The title compound was prepared in the same manner as that in example 2, except that 4-aminophenol was used to replace 4-chlorophenol.

1H NMR (300 MHz, DMSO-d6) ppm 5.07 (br. s., 2H) 5.97-6.12 (m, 3H) 6.60 (m, J=8.80 Hz, 2H) 6.79 (d, J=7.33 Hz, 1H) 6.85 (m, J=8.50 Hz, 2H) 7.25 (t, J=8.21 Hz, 3H)

Example 17

Preparation of Compound Yhhu-1151 (5-(3-pyridinemethoxy)-2,4-diaminoquinazoline)

The title compound was prepared in the same manner as that in example 1, except that 3-pyridinemethanol was used to replace methanol.

1H NMR (300 MHz, DMSO-d6) ppm 5.33 (s, 2H) 6.15 (br. s., 2H) 6.68 (d, J=7.92 Hz, 1H) 6.79 (d, J=8.21 Hz, 1H) 7.28-7.39 (M, 2H) 7.39-7.47 (m, 1H) 7.92 (s; 1H) 8.51-8.61 (m, 1H) 8.73 (s, 1H)

Example 18

Preparation of Compound Yhhu-1152 (5-(4-methoxyphenoxy)-2,4-diaminoquinazoline)

The title compound was prepared in the same manner as that in example 2, except that 4-methoxyphenol was used to replace 4-chlorophenol.

1H NMR (300 MHz, DMSO-d6) ppm 3.77 (s, 3H) 6.32 (d, J=7.92 Hz, 1H) 6.96-7.07 (m, 3H) 7.12-7.21 (m, 2H) 7.34 (br. s., 2H) 7.50 (t, J=8.21 Hz, 1H) 8.17 (br. s., 1H) 8.59 (br. s., 1H)

Example 19

Preparation of Compound Yhhu-1411 (5-n-octyloxy-2,4-diaminoquinazoline)

The title compound was prepared in the same manner as that in example 1, except that n-octanol was used to replace methanol.

1H NMR (300 MHz, CHLOROFORM-d) ppm 0.82-0.94 (m, 3H) 1.22-1.43 (m, 6H) 1.43-1.57 (m, 2H) 1.84-1.95 (m, 2H) 1.96-2.09 (m, 2H) 4.12 (t, J=6.60 Hz, 2H) 4.93 (br. s., 2H) 5.62 (br. s., 1H) 6.53 (d, J=8.21 Hz, 1H) 7.02 (d, J=8.50 Hz, 1H) 7.44 (t, J=8.21 Hz, 1H) 7.58 (br. s., 1H)

Example 20

Preparation of Compound Yhhu-1412 (5-isoamyloxy-2,4-diaminoquinazoline)

The title compound was prepared in the same manner as that in example 1, except that isoamylol was used to replace methanol.

1H NMR (300 MHz, CHLOROFORM-d) ppm 1.01 (d, J=6.60 Hz, 6H) 1.45-1.73 (m, 1H) 1.73-1.89 (m, 2H) 4.15 (t, J=6.46 Hz, 2H) 4.92 (br. s., 2H) 5.59 (br. s., 1H) 6.54 (d, J=7.70 Hz, 1H) 7.03 (d, J=9.08 Hz, 1H) 7.44 (t, J=8.25 Hz, 1H) 7.61 ((br. s., 1H)

Example 21

Preparation of Compound Yhhu-1413 (5-neooamyloxy-2,4-diaminoquinazoline)

The title compound was prepared in the same manner as that in example 1, except that neoamylol was used to replace methanol.

1H NMR (300 MHz, CHLOROFORM-d) ppm 1.03-1.19 (m, 9H) 1.86 (br. s., 2H) 3.79 (s, 2H) 4.87 (d, J=2.20 Hz, 2H) 6.53 (d, J=7.98 Hz, 1H) 7.03 (d, J=8.53 Hz, 1H) 7.44 (t, J=8.25 Hz, 1H)

The Inhibitive Activity Test of the Quinazoline Compounds of the Present Invention Against Dengue Virus Serotype II and Hepatitis C Virus of Flaviviridae:

The test results of the inhibitive activity of the quinazoline compounds of the present invention against dengue virus serotype II and Hepatitis C virus of Flaviviridae are listed in table 1.

TABLE 1

The test results of the inhibitive activity against dengue virus serotype II and Hepatitis C virus

| compound | BHK-DV2 (replication) IC50 (μM) | Huh7.5.1-HCV (replication) IC50 (μM) |
|---|---|---|
| Yhhu-0967 | 0.76 | 5.73 |
| Yhhu-0968 | >5 | |
| Yhhu-0969 | 1.12 | |
| Yhhu-0970 | 0.43 | 3.18 |
| Yhhu-1035 | 1.97 | 4.75 |
| Yhhu-1036 | 0.009 | 1.23 |
| Yhhu-1041 | 7.13 | 12.33 |
| Yhhu-1046 | 0.34 | 2.36 |
| Yhhu-1053 | 0.38 | 0.79 |
| Yhhu-1056 | >25 | 0.98 |
| Yhhu-1145 | 0.11 | 2.34 |
| Yhhu-1146 | >25 | 5.13 |
| Yhhu-1147 | 0.10 | 4.69 |
| Yhhu-1148 | 0.04 | 3.12 |
| Yhhu-1149 | 0.16 | 3.94 |
| Yhhu-1150 | 0.49 | 7.25 |
| Yhhu-1151 | 0.43 | 7.84 |
| Yhhu-1152 | 3.11 | 24.67 |
| Yhhu-1411 | 0.18 | 1.57 |
| Yhhu-1412 | 0.10 | 1.74 |
| Yhhu-1413 | 0.16 | 3.75 |

BHK-DV2-Replication Determination:

BHK cells were inoculated on a 96-well plate. 24 hours later, DV2 viruses were added to infect for 2 h (MOI=0.05), and then viral liquid was washed away. After fresh culture medium was replaced, compounds with different concentrations were added respectively, including infection control without addition of compounds and normal MK control free from infection. After 4 days culture, the supernatant of culture fluid was sucked and centrifuged at 1000RCF for 5 min to remove the cell precipitate. Virus RNA was extracted from the supernatant by using a kit, and then reverse transcriped to be as cDNA, which was evaluated by qPCR method to determine the copy number of the virogene group in the supernatant.

Huh7.5.1-HCV Determination:

Huh7.5.1 cell, which is currently the only cell model which can be in vitro infected by HCV viruses, can be infected by HCV viruses in vitro, and generates infective progeny viruses. J399EM is a HCV full-length mutant strain transfected by EGFP, and can generate viruses which have the same infectivity as wild-type JFH-1. Meanwhile, NS5A-EGFP fusion protein fluorescence can be observed directly in the infected cells by inserting the EGFP coding sequence into NS5A region. In this experiment, Huh7.5.1 cells were inoculated on a 96-well plate and cultured under 5% $CO_2$ at 37° C. for 24 h. Huh7.5.1 cells were infected by J399EM virus supernatant (moi≈0.1). Meanwhile, cell control wells free from infection were included. The infected cells were washed with PBS after 8 h infection. Samples with different concentrations were added into Huh7.5.1 cells infected by J399EM viruses. Each concentration was set double wells, and control well without sample was included. The tested samples were diluted to six gradient concentrations and added respectively, and the cells were cultured for another 72 h. After the cells were treated by the samples for 72 hours, the relative intensity of fluorescence (RFU) was recorded at an excitation wavelength of 488 nm and an emission wavelength of 516 nm on a fluorescent ELISA Reader to detect the inhibition effect of the samples against HCV. The inhibition rate against HCV virus was calculated according to equation.

The above experimental results show that the compounds of the present invention have high inhibitive activities against dengue virus serotype II and Hepatitis C virus. The inhibitive effect of the compounds on the copy number of the viruses in the culture supernatant of the BHK infected by DV2 directly reflects the inhibitive effect of the compounds against the generation of progeny viruses. In the HCV detection, the inhibitive effect of the compounds against intracellular replication of the HCV viruses can be visually determined via fluoroscopy. Meanwhile, as the only cell model which can currently be infected in vitro, Huh7.5.1 cell model infected by HCV viruses can maximumly reproduce the infection and replication process of Hepatitis C virus in vivo. Through above experiments, we have found that the compounds in table 1 exhibit excellent inhibitive effects against the two different viruses with IC50<1 μM. Compared with the common control compounds, such as, mycoplienolic acid and broad spectrum antivirotic Ribavirin, the half effective inhibitive concentrations thereof against HCV virus tested in vitro are 1.25 μM and 20 μM respectively. As dengue virus serotype II and Hepatitis C virus both belong to Flaviviridae, it has showed that the compounds of the present invention have excellent inhibitive activity against flaviviridae virus The compounds according to the present invention exhibit excellent inhibitive activity against flaviviridae virus. The compounds of the present invention can be used to prepare effective medicaments for treating diseases caused by flaviviridae virus, especially Hepatitis C virus and Dengue fever virus.

The invention claimed is:

1. A method for inhibiting flaviviridae virus, wherein the method comprises administration of an effective amount of a quinazoline compound of formula I or a physiologically acceptable salt thereof to a subject needed to be treated,

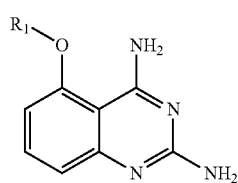

I wherein, $R_1$ is hydrogen, unsubstituted or substituted C1-C10 alkyl, unsubstituted or substituted C3-C10 cycloalkyl, trifluoromethyl, unsubstituted or substituted phenyl, unsubstituted or substituted heterocyclic group, or unsubstituted or substituted fused ring group;

the substituents upon substitution are selected from the group consisting of C1-C10 alkyl, C1-C10 alkoxy, halogen, hydroxy, nitro, carboxy, C6-C10 aryl, phenolic group, amino, amino substituted with C1-C10 hydrocarbyl, heterocyclic group and trifluoromethyl;

the heterocyclic group is a 3- to 7-membered monocyclic ring or a 8- to 10-membered bicyclic ring, which may contain 1 to 3 heteroatoms selected from the group consisting of N, O and S.

2. The method according to claim 1, wherein, $R_1$ is unsubstituted or substituted C1-C10 alkyl, unsubstituted or substituted C3-C10 cycloalkyl, trifluoromethyl, or unsubstituted or substituted phenyl;

the substituents upon substitution are selected from the group consisting of C1-C10 alkyl, C1-C10 alkoxy, halogen, hydroxy, nitro, carboxy, C6-C10 aryl, phenolic group, amino, amino substituted with C1-C10 hydrocarbyl, heterocyclic group and trifluoromethyl;

the heterocyclic group is a 3- to 7-membered monocyclic ring or a 8- to 10-membered bicyclic ring, which may contain 1 to 3 heteroatoms selected from the group consisting of N, O and S.

3. The method according to claim 2, wherein, the quinazoline compound is selected from the group consisting of:

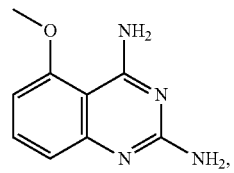

Yhhu-0967

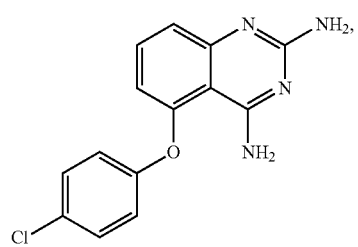

Yhhu-0968

Yhhu-0969
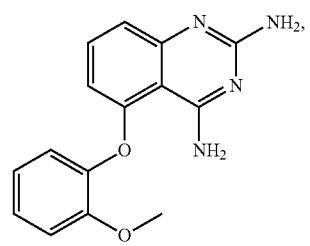
Yhhu-0970
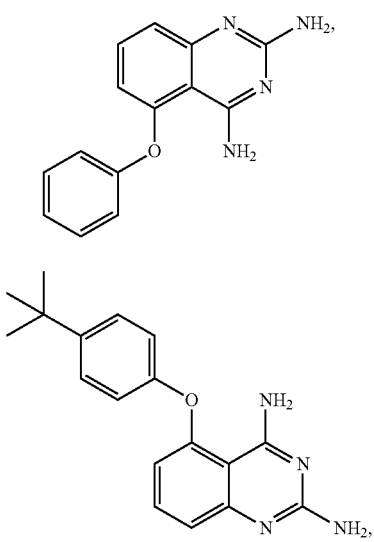
Yhhu-1035
Yhhu-1036
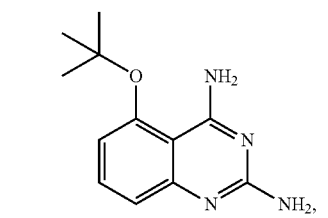
Yhhu-1041
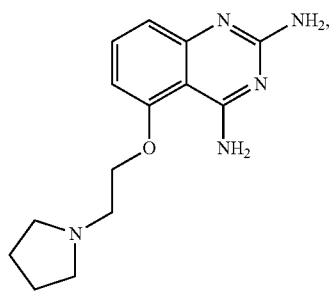
Yhhu-1046
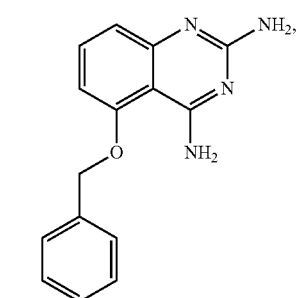
Yhhu-1053
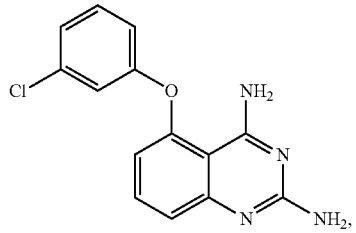
Yhhu-1056
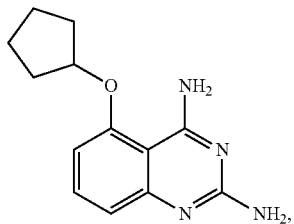
Yhhu-1145
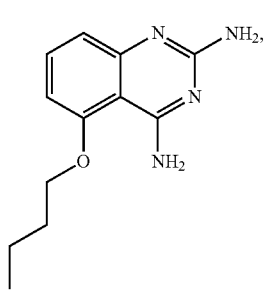
Yhhu-1146
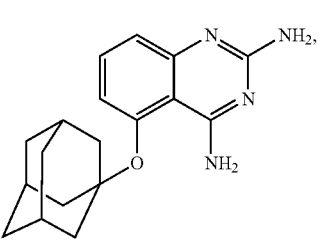
Yhhu-1147
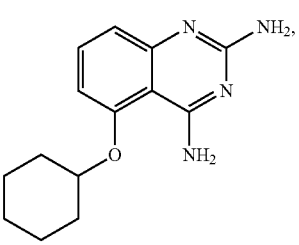
Yhhu-1148
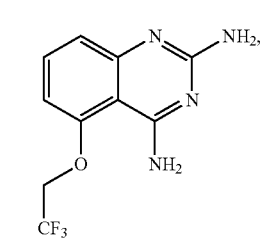

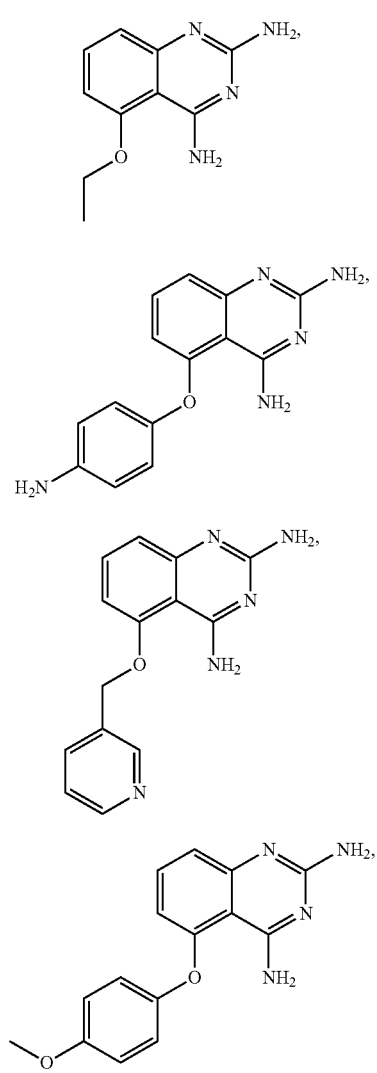
Yhhu-1149
Yhhu-1150
Yhhu-1151
Yhhu-1152
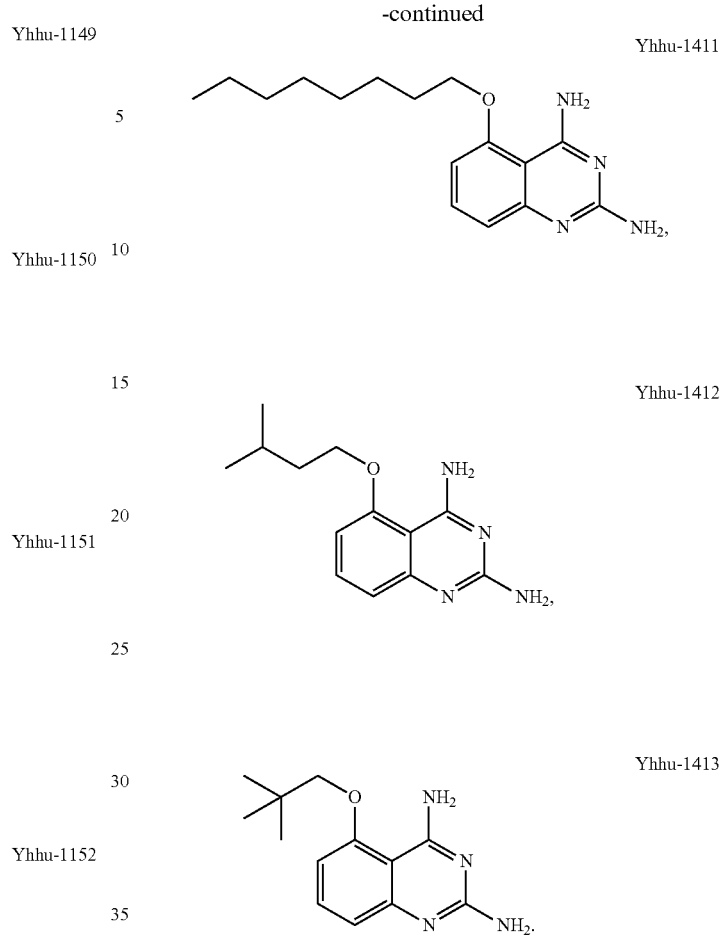
Yhhu-1411
Yhhu-1412
Yhhu-1413
4. The use according to claim 1, wherein, the virus is selected from the group consisting of Dengue fever virus and Hepatitis C virus.
* * * * *